United States Patent [19]

Beaudet

[11] Patent Number: 5,073,324
[45] Date of Patent: Dec. 17, 1991

[54] METHOD FOR SETTING OPHTHALMIC LENSES IN GOGGLES

[76] Inventor: Manon J. Beaudet, 6664, 1st Avenue, Montreal, Quebec, Canada, H1Y 3B1

[21] Appl. No.: 659,630

[22] Filed: Feb. 25, 1991

[30] Foreign Application Priority Data

Mar. 8, 1990 [GB] United Kingdom ............... 9005230

[51] Int. Cl.⁵ .................. B29C 39/12; B29D 11/00
[52] U.S. Cl. .................................... 264/255; 2/426; 264/1.7; 264/262; 264/263
[58] Field of Search .............. 264/1.7, 1.8, 255, 262, 264/263; 2/426, 437, 438, 440, 441; 156/99, 107

[56] References Cited

U.S. PATENT DOCUMENTS

| 2,355,015 | 8/1944 | Splaine et al. | 2/437 |
| 2,373,388 | 4/1945 | Fischer | 2/440 |
| 3,415,595 | 12/1968 | Nelson | 2/426 |
| 4,290,673 | 9/1981 | Yamamoto | 2/437 |

FOREIGN PATENT DOCUMENTS

| 1004403 | 1/1977 | Canada | 2/440 |

Primary Examiner—James Lowe
Attorney, Agent, or Firm—Roland L. Morneau

[57] ABSTRACT

A method for setting an ophthalmic lens in a pair of goggles having a flat front transparent lamina for permitting vision and also having a shielding rim surrounding the lamina extending towards the face of the wearer for the abutment thereon is characterized by a lens secured inside the shielding rim adjacent the lamina. The ophthalmic lens has a flat plane adjacent the lamina separated therefrom by an air gap. A first silcone-base caulking is deposited between the periphery of the lens and the shielding rim up to a level substantially corresponding to the thickness of the air gap. This first caulking has a viscosity sufficiently sag-proof to maintain the caulking at the periphery of the gap during its hardening. A second caulking having a lower viscosity is deposited on the top of the first caulking up to a level corresponding to the top of the lens. The caulking is selected to be free of toxic and corrosive gas. The lens has a peripheral groove to improve the adherence of the second caulking.

8 Claims, 2 Drawing Sheets

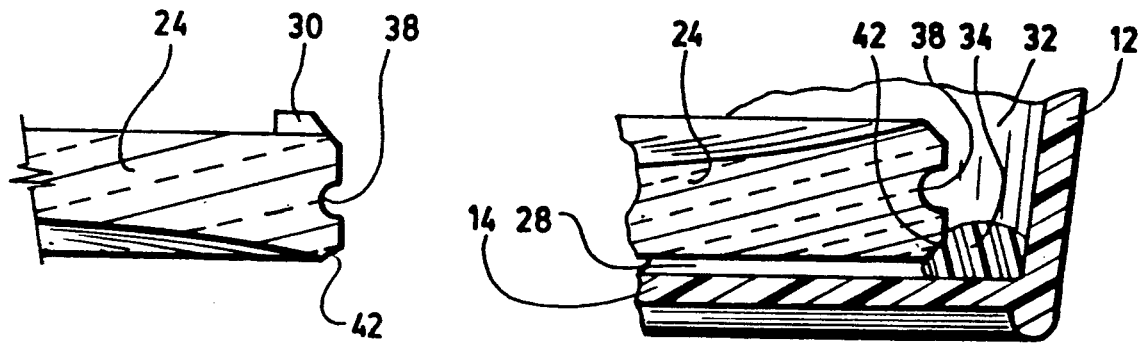
Fig.4
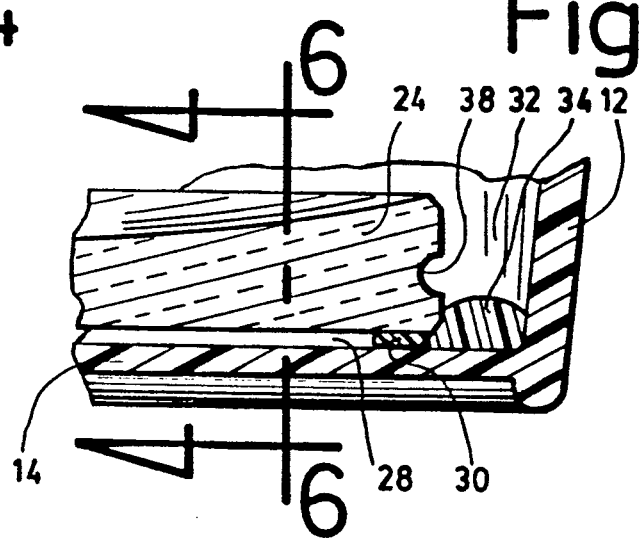
Fig.6
Fig.5
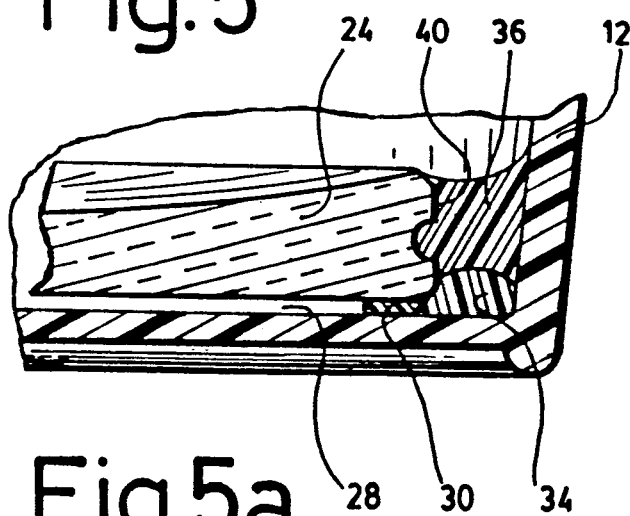
Fig.5a

METHOD FOR SETTING OPHTHALMIC LENSES IN GOGGLES

BACKGROUND OF THE INVENTION

1. Field of the Invention

The invention relates to the adaptation of common goggles into goggles having ophtalmic lenses. In particular, it is directed to a method of setting an ophtalmic lens having a plane and a curved surface inside the rim of the goggles.

2. Prior Art

Many attempts have been made to provide goggles with the desired ophthalmic corrections.

In U.S. Pat. No. 2,333,198 Riddel proposes to make use of a clip to hold a magnifying lens inside a pair of goggles. Chan in U.S. Pat. No. 3,051,957 has a spectacle supporting device inside a face mask for diving. Such devices are not reliable and do not offer the needed confort for most sporting activities.

Canadian patent 1,004,403 describes an eye protector making use of a molded lens. Molded lenses offer an inadequate quality of vision. A separate lens is also proposed but is snapped in a peripheral groove.

Quality vision lenses are always surfaced by machines and cannot be the result of a molding operation. Curved and flat surfaces of ophtalmic lenses require high precision and must be grounded within very small tolerances which cannot be achieved by molding. Precision of a quarter of a diopter is a minimal tolerance. Corrections such as astigmatism further complicates the production of ophthalmic lenses.

The proposed solution consists in the combination of a surfaced lens to about any types of goggles which provides a vision comparable to ordinary spectacles but which are solidly secured to the goggles, without allowing water or gas infiltration. The installation of such a lens is not obvious.

It is the object of the present invention to install corrective lenses in goggle which provide the required optical and physical performances.

The ophthalmic lenses must be suitably mounted onto most of the goggles without any motion relative to the goggles to maintain the same line of sight without lateral and angular displacement or relative rotation. The interpupillary distances determine with precision the required separation between the optical axis of both lenses.

Considering that most of the goggles have a front protective lamina which is not circular and which is surrounded by a funnel or conical type shielding, the setting of an ophthalmic lens with the required precision is not obvious. The expected results are further complicated by the fact that the front lamina of goggles which are made of molded plastic are not optically flat and cannot be directly glued to the ophthalmic lens.

SUMMARY OF THE INVENTION

The present invention is directed to a method for setting an ophthalmic lens in a pair of goggles and to the goggles resulting from that method. The goggles used in this method have flat front transparent lamina for permitting vision and a conical shielding rim surrounding the lamina and extending towards the face of a wearer for abutment thereon. The method comprises, laying an ophthalmic lens having a curved and a flat plane on the lamina, the flat plane of the lens being positioned adjacent the lamina and separated by an air gap. The lens has a peripheral wall substantially perpendicular to the flat plane of the lens and slightly smaller than the rim to maintain a substantially uniform peripheral interspace between the periphery of the lens and the rim. The method includes depositing in the interspace a first silicone-base caulking to cover the periphery of that gap. The caulking has a viscosity sufficiently high to be sag-proof so as to maintain the caulking at the periphery of the gap during its hardening and then depositing in the interspace, over the first caulking, a second silicone-base caulking to cover at least a part of the peripheral wall. The second caulking has a viscocity lower than the first caulking. Subsequentally, the second caulking is allowed to dry during a predetermined period of time.

BRIEF DESCRIPTION OF THE DRAWING

FIG. 4 is a cross-sectional view along line 4—4 of FIG. 3, FIG. 5 is a cross-sectional view of a portion of the ophthalmic lens mounted in the goggle at one stage of the setting method, FIG. 5a is a view corresponding to FIG. 5 but at a subsequent stage of the method, and FIG. 6 is a cross-sectional view along line 6—6 of FIG. 5.

DETAILED DESCRIPTION OF THE INVENTION

Figure 1:
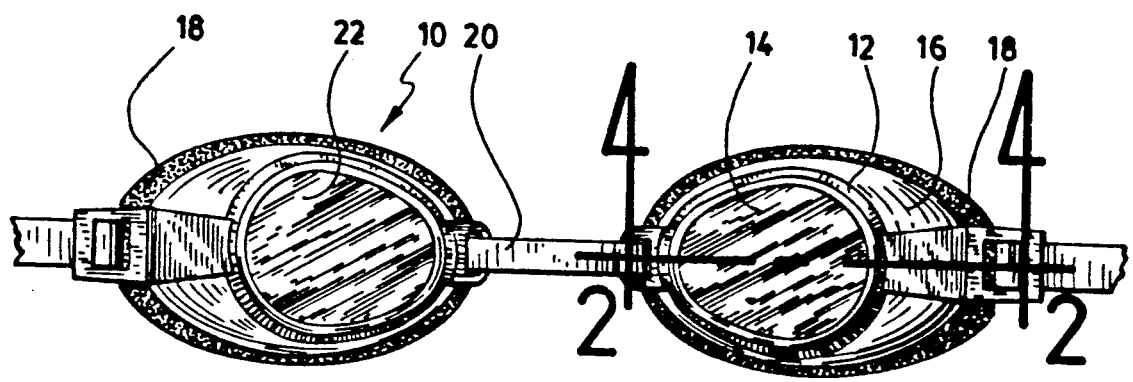
FIG. 1 is a front view of a pair of goggles inside of which an ophthalmic lens is mounted according to the invention.
Figure 2:
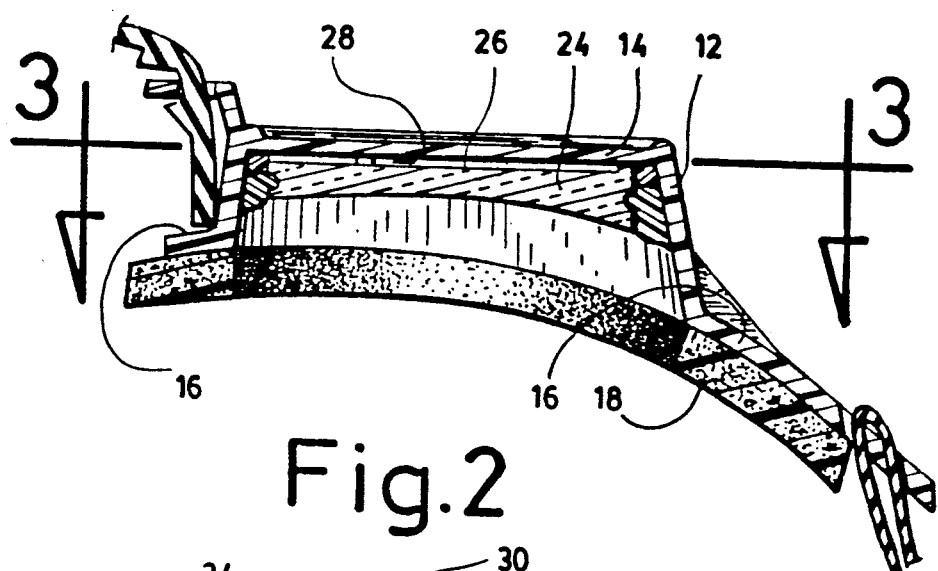
FIG. 2 is a cross-sectional view along line 2—2 of FIG. 2.

FIG. 1 illustrates a pair of goggles 10 having a shielding rim 12 surrounding a flat, front, transparent lamina 14. The shielding rim 12 has a flange 16 adapted to extend over the periphery of the orbit of the eye. The flange 16 is usually covered by a foam rubber 18 adapted to seal the orbit of the eye against liquid or gas. The distance between each lamina 14 and 22 of the goggles 10 is adjusted by the band 20 to correspond to the distance due to the interpupillary distance of the wearer. In the case of commonly known goggles having a flat lamina 14, the distance between the center of the two laminas is not critical but will be so with the addition of ophtalmic lenses such as the lens 24. Such a lens is required for good vision if a person wearing the goggles usually wears spectacles or contact lenses.

The goggles which are commercially available are made of molded plastic. Goggles having a molded lens instead of the lamina 14 has been experimented but was found unsatisfactory to provide an excellent vision for the wearer. Molding processes cannot give to an optical surface the degree of precision required in optometry. If a plastic lens would be molded in goggles, both the internal and external surfaces would have to be grounded with an accurate degree of precision. No instruments are available to provide the surface needed inside a shielding rim such as 12.

The present invention consists in setting a lens made of glass or plastic inside the shielding rim 12 adjacent the flat lamina 14. In order to provide an equally good vision for swimmers, inside and outside the water, a plano-convex or plano-concave lens must be used with the flat surface facing outwardly.

In the present embodiment, a plano-concave lens is illustrated in the drawings. The flat surface 26 of the lens 24 cannot be made in full contact with the lamina 14 because the latter being molded does not provide an optically flat surface and accordingly with the flat surface 26 of the lens 24, pockets of air therebetween would create interference rings or fringes.

Figure 3:
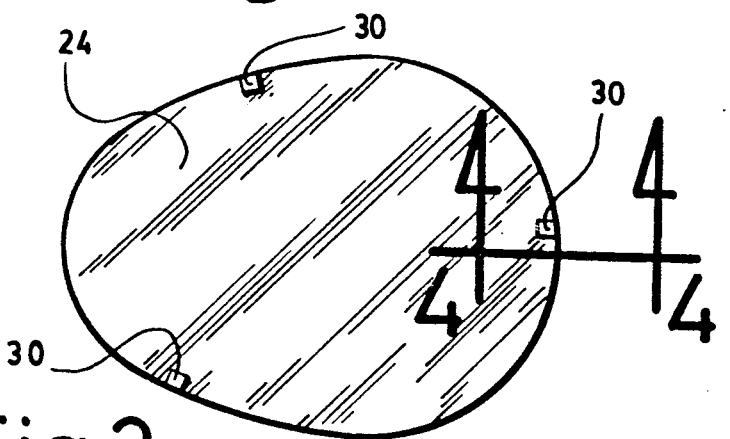
FIG. 3 is a front view of an ophthalmic lens on which three spacers are mounted.

In order to obviate this latter phenomenon, the flat surface 26 of the lens 24 is kept at a distance from the lamina 14 to maintain an air gap therebetween. The air gap 28 is obtained by securing three thin spacers 30 on the flat surface of the lens 24 as particularly shown in the FIGS. 3 and 4. The thickness of the surface is just sufficiently thick to be sure that the flat surface 26 will never be in contact with the lamina 14.

According to the invention, ophthalmic lenses can be mounted in any available goggles on the market. As particularly illustrated in FIG. 3, the periphery of the lens is adapted to fit the inner surface of the lamina while being surrounded by the shielding rim 12. Although such a perimeter varies according to the type of goggles selected, an interspace is left all around the lens 24 in order to introduce an adhesive all around the lens which will hold the latter to the shielding rim 12 and the lamina 14. Because the ophthalmic lens 24 is spaced from the lamina 14, any adhesive dropped into the interspace 32 adjacent the shielding rim 12, has a tendency to flow between the lens 24 and the lamina 14 around the whole periphery of the lens except the portion corresponding to the spacers 30. In the method of setting the lens 24, at least two steps are needed for the securing of the lens in its proper place. An adhesive of the type of a silicone-base caulking is used and such a caulking must have a viscosity which will prevent the latter from flowing under the lens to any substantial distance. In fact, the caulking selected is referred to as sag-proof for maintaining the caulking at the periphery at the air gap during its hardening. The viscosity of such a caulking is generally in excess of 300 poises and preferably 350 poises. This first caulking is just sufficiently thick to cover the whole periphery of the air gap 28 as particularly shown in FIGS. 5 and 6. Caulking number 3145 RTV produced by Dow Corning Corporation of Midland Mich., U.S.A., have been found suitable for that purpose. Considering that the interspace 32 has a peripheral width of about 2 millimeters, the adhesive is preferably dropped with a hypodermic syringe which allows the lens to remain centered and which also allows the proper quantity of the adhesive to be inserted. A hardening period of about 24 hours is needed to assure the maintenance of the centering of the lens under all future normal conditions of use of the goggles. It is pointed out that such goggles when used for swimming are frequently under stress and particularly in cases such as for diving.

The next step consists in adding another adhesive which has a lower viscosity, has the property of hardening and providing a solid adherence while the volume of the adhesive is relatively large. Such a lighter caulking 36 is less bound to retain bubbles than a thick one and accordingly to produce a better adherence over all the contacting surfaces.

The use of a single adhesive having a low viscocity would flow through the gap and accordingly would fail to provide a good line of sight for the wearer. On the other hand, the use of a caulking such as 34 having a high viscosity if used alone, could not be expected to provide the needed adherence for maintaing the position of the lens 24 inside the goggle. In addition, it would not be expected to harden throughout.

The adhesive 36 selected for the present invention is of the type sold by Dow Corning Corporation under number 3140 RTV. This adhesive is also preferably introduced by an hypodermic needle.

It is pointed out, at this stage, that many types of glues available on the market cannot be used for the particular purpose of this invention. Some of the glues which produces certain chemical vapors or ordors may be detrimental to the eyesight and are generally forbidden by the government regulations. Such restrictions apply to epoxy glue. The fact that the eye is completely enclosed by the goggles means that the environment must be strictly free of any harmful compounds.

The retention of the adhesive 36 with lens 24 is improved by providing the peripheral wall 40 of the lens with a peripheral groove 38. The fluidity of the adhesive 36 will allow the latter to flow evenly inside the groove 38 and accentuate the gripping of the lens.

In order to provide an additional retention factor between the adhesive 36 with the lens and the rim 12, the top level of the adhesive 36 substantially corresponds to the apex of the peripheral wall 40.

Although the invention has been previously described as the plano-concave lens the same applies to a plano-convex lens although the peripheral wall must be maintained at a height of about 4 millimeters.

The present invention has been particularly contemplated for aquatic goggles and for this reason, the glue must have certain characteristics which facilitates the setting of the ophthalmic lens but also must meet certain standards of resistance as well as being resistant to harsh environments such as ozone, moisture and weathering. Also, considering the flexibility of the goggles and the stress applied to them, the adhesive needs to remain rubbery within substantially large limits that is from cold water to rather hot water.

The present invention is not restricted to aquatic goggles and may be applied to various other conditions such as for firemen fighting fires, welders facing electric sparks and any other situations where goggles are needed with an ophthalmic correction for the eyes.

In order to provide a larger adhesive surface for the adhesive 34, a chamfer 42 is provided at the intersection of the peripheral wall 40 and the flat surface 26 of the lens.

It is pointed out that a lens having a proper correction for the eyes frequently needs a correction for the astigmatism. Such a correction cannot be obtained from other means than a polished lens.

If adherence of the caulkiing used needs to be improved for some reason such as the area of the surfaces in contact with the adhesives, a primer corresponding to the caulking used is applied on the periphery of the lens and inside the shielding rim.

The present invention has accordingly solved the many problems inherent to the combinations of an ophthalmic lens with a pair of goggles. Such difficulties includes the elimination of air bubbles in the adhesive, the problem created by the mounting of two parallel surfaces and the drying of the adhesives.

It is pointed out that the present method has not affected the resistance and the quality of the goggle per se although there was a need to work within very small surfaces and cavities.

I claim:

1. A method for setting an ophthalmic lens in a pair of pre-assembled goggles having a flat front transparent lamina for permitting vision and a conical shielding rim surrounding said lamina and extending toward the face of a wearer for a abutment thereon, said method comprises, laying an ophthalmic lens having a curved and a flat plane, the flat plane of the lens being positioned adjacent said lamina and separated by a thin flat air gap for preventing the lent from touching the lamina, the lens having a peripheral wall substantially perpendicular to the flat plane of the lens and slightly smaller than the rim to maintain a substantially uniform peripheral interface between the periphery of the lens and the rim, depositing in said interface a first silicone-base caulking to cover the periphery of said gap, said first caulking having a viscosity sufficiently high to be sag-proof for maintaining said caulking at the periphery of said gap during its hardening period, depositing in said interface, over said first caulking, a second silicone-base caulking to cover at least a part of said peripheral wall, said second caulking having a viscosity lower than the first caulking, and allowing said second caulking to dry during a predetermined period of time.

2. A method as recited in claim 1, wherein said peripheral interspace has a thickness of about 2 millimeters.

3. A method as recited in claim 1, wherein the wall of the lens is provided with a peripheral groove, the viscosity of said second caulking adapted to flow into said groove.

4. A method as recited in claim 3, wherein the peripheral wall is about 4 mm high and has a peripheral groove of about 1 to 2 mm, the caulking having viscosity of less than 300 poises.

5. A method as recited in claim 2, wherein the lens is provided with a chamfer between said wall and said flat plane.

6. A method as recited in claim 2, including depositing a third caulking over said second caulking to fill said interspace to a level corresponding to the edge of the wall contiguous with the curved plane.

7. A method as recited in claim 2, applying a primer on said wall and rim prior to the depositing of the first and second caulking.

8. A method as recited in claim 1, which comprises securing spacers on the periphery of said lens, for maintaining said lens in spaced relationship with said lamina.

* * * * *